United States Patent [19]

Barrett

[11] Patent Number: 4,706,661

[45] Date of Patent: Nov. 17, 1987

[54] WOUND CLOSURE AND OBSERVATION DEVICE HAVING A NO-CONTACT PROTECTIVE COVERING

[76] Inventor: David M. Barrett, P.O. Box 1693, Oklahoma City, Okla. 73101

[21] Appl. No.: 925,783

[22] Filed: Oct. 31, 1986

[51] Int. Cl.[4] .............................................. A61F 13/00
[52] U.S. Cl. ................................................... 128/155
[58] Field of Search ........................ 128/155, 157, 132

[56] References Cited

U.S. PATENT DOCUMENTS 4,053,053 10/1977 Tumangday ........................ 128/155
4,614,183 9/1986 McCracken ........................ 128/155

Primary Examiner—Gregory E. McNeill

[57] ABSTRACT

In a protective wound-closing device, a plurality of adhesive backed planar pads arranged in a common plane are normally supported by a manually operated control. The control spreads the position of the respective pads in lateral directions with respect to each other for contact with a patient's skin around a wound; release of the control member from the pads permits a resilient shield member joining the pads to each other to darw opposing edges of a wound toward each other while the central overlying portion of the transparent resilient material shields the wound from contact with foreign matter while permitting air circulation and medication between the elastic shield and the surface of the wound as well as permitting observation of the wound without the necessity of removing the protective device.

11 Claims, 9 Drawing Figures

WOUND CLOSURE AND OBSERVATION DEVICE HAVING A NO-CONTACT PROTECTIVE COVERING

This invention relates to medicinal supplies generally referred to as first aid and more particularly to a wound-closing device for cuts through the skin.

DESCRIPTION OF THE PRIOR ART

Most surgical bandages or adhesive strips of the first aid type have usually comprised a singular section or length of material having a backing sheet centrally perforated between its ends for ventilation above an overlying resilient pad with adhesive material on respective opposing end portions of the bandage. While such bandages are satisfactory for the most part, they have the disadvantage of not being easily placed, particularly where the wound is a cut with edges which need to be drawn toward each other in juxtaposition. Further such bandages which cover the wound do not permit ease of application of medication, and observation and tend to cling to a bleeding wound, resulting in reopening the wound by removing the scab when dressing the injury.

This invention provides a device which eliminates most of the abovenamed disadvantages by having the capability of placement by remote control of the adhesive strips or sections which tend to close a wound and which permit visual observation thereof and during healing.

SUMMARY OF INVENTION

In one embodiment a pair of rectangular sections or pads having one surface coated with adhesive material are secured together in parallel spaced-apart relation by an equal length resilient strip of material, preferably formed from transparent material. A handle member characterized by opposing flange strips coextensive with the pads or strips and connected with angular members which engage the pads or strips for placing the latter over a wound.

In another embodiment a plurality of adhesive pads or strips are similarly resiliently secured in spaced relation in a common plane and are individually attached to a patient's skin by spreading handle members converging toward an overlying control and release point.

The principal objects of this invention are to provide a wound protecting device which is self-adhering, tending to draw opposing edges of a wound toward each other from opposing positions laterally of the boundary of the wound; provide visual inspection of the wound; facilitate medicating and cleaning the wound without removing the device; achieve a consistent, even pressure along the boundaries or periphery of the wound; does not constrict blood circulation or capillary flow; and aerates the wound during healing.

BRIEF DESCRIPTION OF THE DRAWINGS

Like characters of reference designate like parts in these figures of the drawings in which they occur.

In the drawings.

Figure 1:
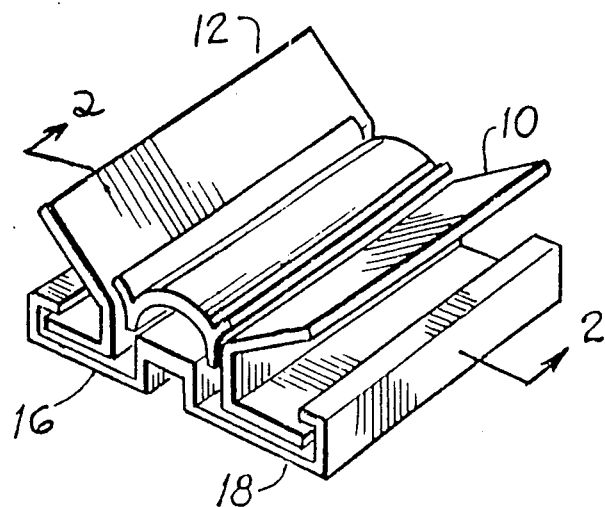
FIG. 1 is a perspective view of one embodiment of the device.

The reference numeral 10 indicates one embodiment of the device which is rectangular in general configuration. The device 10 comprises a handle or control portion 12 and a base or pad portion 14. The base portion 14 includes rectangular planar pads or strips 16 and 18 of substantially equal width and a desired thickness, relatively thin, when compared with the pad perimeter dimensions.

Each of the pads are provided with an underlying layer of adhesive 20. The adhesive being capable of adhering to tne skin of a patient. The longitudinal confronting edge surfaces 22 and 24 of the respective pads are secured to opposing longitudinal legs of a U-shape in transverse section coextensive strip of transparent resilient or elastic material 26. The elastic material 26 normally draws the confronting edge surfaces 22 and 24 toward each other. The major portion 27 of the elastic strips is disposed in a plane spaced above the plane common to the pads 16 and 18.

The handle or control means 12 comprises a pair of planar flanges 28 and 30 of selected width, for example, equal to the transverse width of each of the pads and coextensive therewith. Each of the flanges 28 and 30 have longitudinal confronting edges secured to a resilient member 32 coextensive therewith and transversely arcuately bowed upwardly. The same longitudinal edge of both flanges is integrally connected with the leg 34 of a pair of substantially L-shaped depending members. The foot 36 of each L-shaped member contiguously overlies the planar top surface of the respective strips 16 and 18 with the lateral edge surface of each foot 36 opposite its leg removably engaged under an inverted L-shaped hook member 38 longitudinally secured to the outer edge surface of each pad 16 and 18 opposite their resiliently connected edges.

OPERATION

Figure 2:
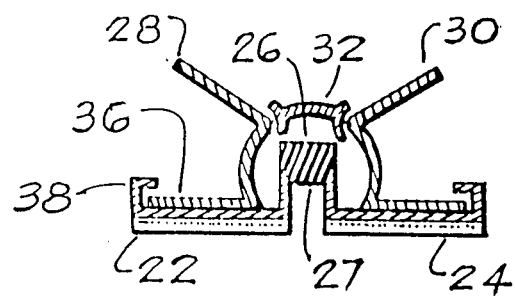
FIG. 2 is a transverse vertical cross section view to a larger scale taken substantially along line 2—2 of FIG. 1.
Figure 3:
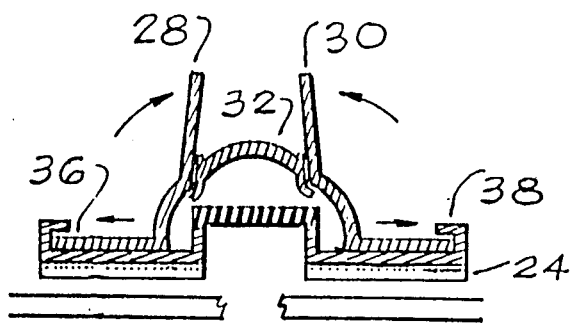
FIG. 3 is a view showing device spread apart by squeezing control handles.
Figure 4:
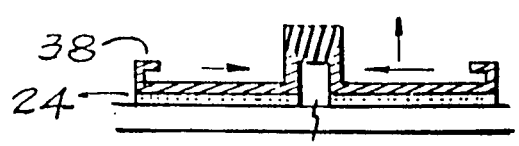
FIG. 4 is a view similar to FIG. 2 illustrating the control handle removal; also showing the pads per se.

In the operation of the embodiments of FIGS. 1-4, assuming the device 10 is packaged or maintained in a sterile condition, being removed from such container at the point of use. The operator grasps the flanges 28 and 30, as between a forefinger and thumb, and manually moves the flanges toward each other in an upward converging action which fulcrums the flanges against the uppermost elastic member 32 forcing the legs of the L-shaped members in opposing directions and spreading the pads 16 and 18 laterally apart to the desired extension of the elastic member, or in accordance with the lateral dimension of the cut.

The operator then places the pads in straddling relation across the area of the wound, such as a cut, with the pads contacting the patient's skin, releases the pressure on the flanges 28 and 30. This allows the L-shaped member foot portions 36 to retract from the contact with the respective hook member 38 and separation of the two components. The elastic strip 26 by its resiliency draws the pads 16 and 18 toward each other in a wound closing action without contact between the elastic strip central portion 27 and the surface of the wound.

Figure 5:
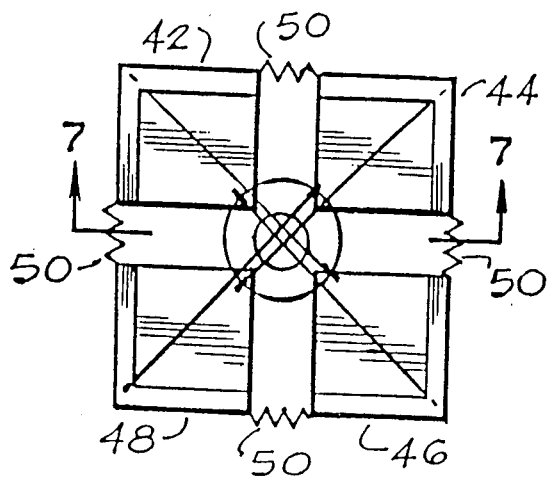
FIG. 5 is a top view of another embodiment.
Figure 6:
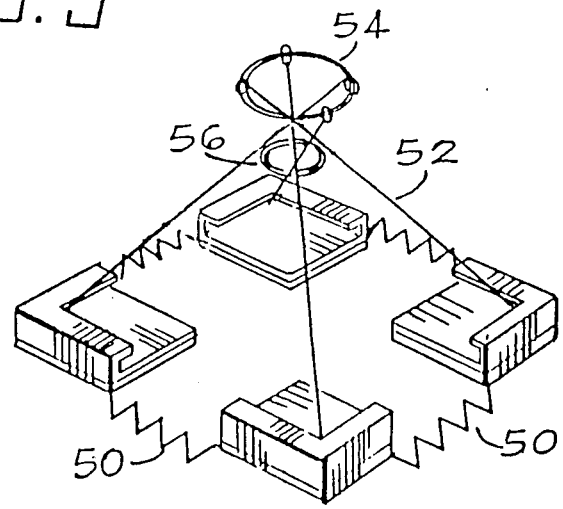
FIG. 6 is a perspective view of the device seen in FIG. 5.
Figure 7:
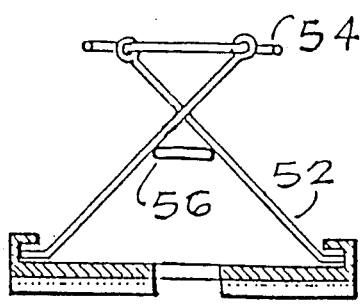
FIG. 7 is a vertical cross section view taken substantially along the line 7—7 of FIG. 5.
Figure 8:
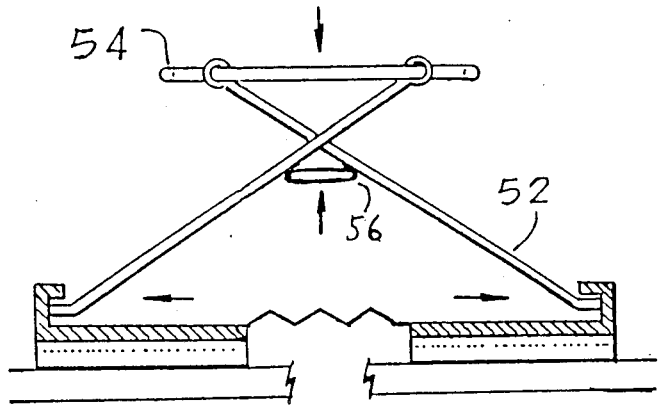
FIG. 8 illustrates the placement of the device on a cross-cut wound.
Figure 9:
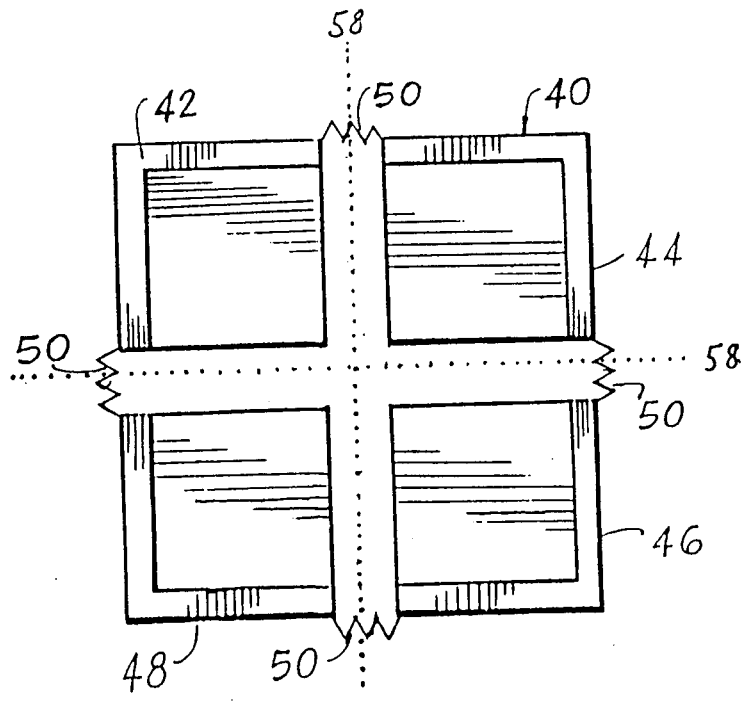
FIG. 9 is a top view of FIG. 7 with the pad spreading control removed.

Referring now more particularly to FIG. 5 through 9, another embodiment of the device indicated generally at 40 comprises a plurality of rectangular pads or strips 42, 44, 46 and 48 of similar adhesive coated material arranged in opposition and normally lying in a common plane. Each of the pads or strips 42-48 are connected together by sections of adhesive material 50 connected with and extending between and similarly tending to draw confronting edges of the several pads toward each other. A plurality of elongated rod-like control arms 52, one for each of the several pads, is connected with a portion of the respective pads removed from a central position between the pads and extends angularly upward toward a common point of convergence spaced above the plane of the pads for connection, in circumferential spaced relation, with the perimeter of a control ring 54. An angular perimeter portion of each pad most remote from a common central point is provided with an angular overhanging hook portion 55 under which the lower most end portion of each arm 52 is engaged. A second control ring 56 surrounds the several arms near the point of convergence for the purpose of spreading apart the ends of the arms and the connecting pads against the resilience of the elastic material 50 or drawing together the pad connected arm ends by movement of the control rings 54 and 56 in a selected up or down direction.

Conversely moving the rings in an opposite direction with respect to each other permits the resilient strips 50 to draw the several pads 42-48 toward a central point in the plane of the pads.

In the operation of the embodiment of FIGS. 5-9, the device 40 is grasped by the control rings 54 and 56 for spreading the pads in lateral or diverging directions. This permits the pads to be selectively positioned on a cross-cut wound indicated by the dotted lines 58. When the several pads contact the patient's skin adjacent the respective several edges of the wound the control rings 54 and 56 are operated to release the arms from contact with the respective angle socket 55 on the respective pad allowing the resilient strips 50 to draw the pads toward each other in a wound closing action.

Obviously the invention is susceptible to changes or alterations without defeating its practicability. Therefore, I do not wish to be confined to the preferred embodiments shown and described in the accompanying drawings.

I claim:

1. A wound closing protective device, comprising:
a plurality or planar pads normally disposed in a common plane,
each planar pad having a coating of adhesive material on one surface;
resilient means secured to confronting edges of said pads for drawing said pads toward each other; and, manually operated control means remote from and a depending portion contactably overlying the several pads for moving the pads in diverging directions.

2. The device according to claim 1 in which:
the resilient means comprises a transparent strip of elastic material.

3. The device according to claim 2 in which:
the major portion of the resilient means is disposed in a plane above the plane of said pads.

4. The device according to claim 3 in which:
the control means comprises at least one handle having an extension frictiona-ly contacting the respective pads.

5. The device according to claim 4 in which:
the handle comprises a pair of oppositely disposed elongated handles pivotally interconnected longitudinally for movement of the handle portions remote from the pivotal connection toward and away from each other for moving said pads in selected directions relative to each other.

6. The device according to claim 5 and further including:
resilient means interposed between and connected with said handles.

7. The device according to claim 4 in which:
the handle comprises a plurality of upright elongated arm members disposed in downwardly diverging relation and releasably connected with said pads.

8. The device according to claim 7 and further including:
a ring member secured to the end portions of said arms opposite said pads.

9. The device according to claim 8 and further including:
other ring means surrounding said arms intermediate their pads for convergent and divergent movement of the end portions of said arms adjacent said pads by movement toward and away from the first said ring member.

10. A wound dressing device having at least two resiliently interconnected adhesive pads normally biased toward each other, comprising:
means contacting and spreading apart the adhesive pads for placement while under spread-apart stress on respective opposing sides of a wound, whereby when released, said pads are biased toward each other to close the wound without contact therewith.

11. In a wound or laceration dressing device including adhesive pads joined at their top by an overlying elastic cover, the improvement comprising: their upper limit in a plane common to all the pads one hand applicator means releasably connected with said pads, whereby when placed on either side of or around a wound or laceration said pads adhesive properties combine with the elastic cover bias tending to close an open wound without contact with the wound.

* * * * *